US006624340B2

(12) United States Patent
Mizutani et al.

(10) Patent No.: US 6,624,340 B2
(45) Date of Patent: Sep. 23, 2003

(54) ABSORBENT ARTICLE HAVING LONGITUDINALLY EXTENDING LEAKAGE PREVENTING WALLS ON TWO SIDES

(75) Inventors: Satoshi Mizutani, Kagawa (JP); Tatsuya Tamura, Kagawa (JP); Yuuki Noda, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/881,865

(22) Filed: Jun. 15, 2001

(65) Prior Publication Data

US 2001/0056268 A1 Dec. 27, 2001

(30) Foreign Application Priority Data

Jun. 19, 2000 (JP) ......................................... 2000-182872

(51) Int. Cl.[7] ............................. A61F 13/15; A61F 13/20
(52) U.S. Cl. ............. 604/358; 604/385.03; 604/385.01; 604/380; 604/385.27; 604/385.28
(58) Field of Search ................................. 604/365, 356, 604/358, 380, 366, 367, 368, 375, 378, 385.01, 385.03, 385.04, 385.05, 385.14, 386, 387, 389, 385.27, 385.28, 385.101

(56) References Cited

U.S. PATENT DOCUMENTS

| | | | | | |
|---|---|---|---|---|---|
| 5,181,563 | A | * | 1/1993 | Amaral | 604/378 |
| 5,312,386 | A | * | 5/1994 | Correa et al. | 604/379 |
| 5,342,342 | A | * | 8/1994 | Kitaoka | 604/385.19 |
| 5,681,302 | A | * | 10/1997 | Melbye et al. | 604/373 |
| 5,921,975 | A | * | 7/1999 | Suzuki et al. | 604/385.17 |
| 5,947,948 | A | * | 9/1999 | Roe et al. | 604/385.23 |
| 5,993,433 | A | * | 11/1999 | St. Louis et al. | 604/385.27 |
| 6,123,694 | A | * | 9/2000 | Pieniak et al. | 604/385.28 |
| 6,126,648 | A | * | 10/2000 | Keck et al. | 604/385.24 |
| 6,186,992 | B1 | * | 2/2001 | Roe et al. | 604/367 |
| 6,193,701 | B1 | * | 2/2001 | Van Gompel et al. | 604/370 |
| 6,235,137 | B1 | * | 5/2001 | Van Eperen et al. | 156/160 |
| 6,290,979 | B1 | * | 9/2001 | Roe et al. | 424/402 |
| 6,315,765 | B1 | * | 11/2001 | Datta et al. | 604/385.24 |
| 6,436,081 | B1 | * | 8/2002 | Wada et al. | 604/385.01 |
| 6,458,113 | B2 | * | 10/2002 | Kashiwagi | 604/385.16 |
| 2002/0062112 | A1 | * | 5/2002 | Mizutani | 604/367 |

FOREIGN PATENT DOCUMENTS

JP    9-503934    4/1997

* cited by examiner

Primary Examiner—Henry Bennett
Assistant Examiner—Kathryn Ferko
(74) Attorney, Agent, or Firm—Darby & Darby (57) ABSTRACT

Disclosed in an absorbent article including a main body and leakage preventing walls. The leakage preventing walls extend longitudinally and lie opposite one another transversely. Each wall is formed of a nonwoven fabric having corrugations, the crests and valleys of which alternate with each other in the longitudinal direction. The nonwoven fabric is provided with an elastic member extending in the longitudinal direction for exhibiting longitudinal shrinking force. The elastic member is adhered to the valleys of the corrugations of the nonwoven fabric with an adhesive. The adhesive is applied to the surface of the elastic member in a band or linear shape continuous in the axial direction of the elastic member and appears regularly or at random at an interval on an arbitrary line which is set on the surface of the elastic member to extend parallel to the axial direction.

5 Claims, 5 Drawing Sheets

ABSORBENT ARTICLE HAVING LONGITUDINALLY EXTENDING LEAKAGE PREVENTING WALLS ON TWO SIDES

BACKGROUND OF THE INVENTION

1. Field of the Invention

The present invention relates to an absorbent article such as a sanitary napkin, a disposable diaper or the like and, more particularly, to an absorbent article having longitudinally extending leakage preventing walls on the two sides.

2. Related Art

In the prior art, there have been developed a variety of absorbent articles including sanitary napkins, urine pads, disposable diapers and the like. These absorbent articles are demanded, when worn, to absorb a liquid waste reliably in a liquid-absorbent layer and to prevent the liquid waste from leaking to the outsides of the absorbent articles. Therefore, some absorbent article has longitudinally extending leakage preventing walls formed on the two sides on the liquid receiving face thereof.

Generally, the leakage preventing walls of the prior art are constructed such that unstretchable hydrophobic sheets extending in the longitudinal direction are joined to a surface sheet of an absorbent article and elastic members extending in the longitudinal direction of the absorbent article are joined to the hydrophobic sheets. By the longitudinal elastic shrinking forces of the elastic members, a longitudinally curving force is caused to act on the absorbent article, and the leakage preventing walls are raised on the liquid receiving side of the absorbent article so that the menstrual blood or the like can be prevented from leaking sideways.

In most of the leakage preventing walls of the absorbent article of the prior art, however, the surface to abut against the skin of a wearer is so flat that the leakage preventing walls come into contact with the skin of a wearer too tight. Moreover, most of them do not provide a soft contact with the skin due to its hard touch feel.

In some absorbent article of the prior art, on the other hand, the leakage preventing walls are formed of a nonwoven fabric which is deformed (formed) into a corrugated shape. The leakage preventing walls of this shape can reduce the contact area with the skin of a wearer so that they can provide a soft feel to the skin, as disclosed in International Unexamined Patent Publication No. 503934/1997, for example. However, since the leakage preventing walls of this disclosure are formed to exhibit the elastic force by themselves, the leakage preventing walls have a low rigidity of their own. Therefore, when the leakage preventing walls are disposed to rise from the surface of the absorbent article, for example, their buckling strength cannot be highly enhanced.

If longitudinally extending elastic members are joined to the nonwoven fabric deformed (or formed) into the corrugated shape, the resulting leakage preventing walls exhibit a high rising force from the liquid receiving side of the absorbent article, so that it becomes difficult for the leakage preventing walls to fall down. However, if these longitudinally extending elastic members are adhered to the corrugated nonwoven fabric with a hot-melt adhesive or the like, the crests of the corrugations are adhered with the adhesive when a pressing force acts on the nonwoven fabric. Therefore, the corrugations of the nonwoven fabric are liable to be kept in a crushed state. As a result, she nonwoven fabric is hardened at the portion where the elastic members are adhered, so that its contact feel with the skin of a wearer is deteriorated.

SUMMARY OF THE INVENTION

The present invention has an object to provide an absorbent article which can realize leakage preventing walls providing a soft touch to the skin of a wearer and which can prevent the adhered portion between the nonwoven fabric forming the leakage preventing wall and the elastic member from being hardened, thereby not to damage the soft feel.

According to an aspect of the invention, there is provided an absorbent article comprising: a main body including a liquid-permeable surface sheet disposed on its liquid receiving side, a back sheet, and an absorbent layer sandwiched between the surface sheet and the back sheet; and leakage preventing walls-disposed on the liquid receiving side-of the main body, the leakage preventing walls extending in a longitudinal direction of the article and lying opposite one another in a transverse direction perpendicular to the longitudinal direction, wherein each leakage preventing wall is formed of a nonwoven fabric having corrugations, the crests and valleys of which alternate with each other in the longitudinal direction, the nonwoven fabric is provided with an elastic member extending in the longitudinal direction for exhibiting longitudinal shrinking force, and the elastic member is adhered to the valleys of the corrugations of the nonwoven fabric with an adhesive, which is applied to the surface of the elastic member in a band or linear shape continuous in the axial direction of the elastic member and appears regularly or at random at an interval on an arbitrary line which is set on the surface of the elastic member to extend parallel to the axial direction.

According to the absorbent article of the invention, the nonwoven fabric forming the leakage preventing wall is molded (or formed) to have the corrugations so that the contact area with the skin of a wearer can be reduced to eliminate the tightness on the skin and to soften the abutment. In addition, the elastic members for exhibiting the shrinking forces in the longitudinal direction are joined to the leakage preventing walls so that the longitudinal shrinking forces act on the leakage preventing walls. As a result, the absorbent article is longitudinally curved to allow the leakage preventing walls to rise easily. Moreover, since the applied adhesive appears intermittently on the arbitrary line extending in the longitudinal direction, the inner faces of the nonwoven fabric other than the valleys of the corrugations hardly contact with the adhesive. Accordingly, the corrugations of the nonwoven fabric are not either crushed or hardened with the adhesive even at the portion having the elastic member, to thereby prevent stiff contact feel with the skin of a wearer. Thus, the leakage preventing walls of the absorbent article can keep the soft feel.

For example, the adhesive may be applied to the surface of the elastic member along such an undulating locus that an amplitude is taken in a direction to intersect the longitudinal direction. Alternatively, the adhesive may be so applied to the surface of the elastic member as to form a helical locus which extends in the longitudinal direction while turning around the elastic member.

Preferably, the undulating locus or the helical locus of the adhesive has a period longer than that of the corrugations of the nonwoven fabric.

With the pitch (i.e., period) of the corrugations of the nonwoven fabric being made small, in the absorbent article of the invention, the leakage preventing walls can be made soft not only in their structure but also in their abutment against the skin of a wearer. In this case, if the period of the undulating locus or the helical locus of the applied adhesive is made longer than that of the corrugations of the nonwoven fabric, the probability for the portions of the nonwoven fabric other than the valleys of the corrugations to come into contact with the adhesive can be lowered to enhance the corrugation crush preventing effect. On the other hand, the individual valleys of the corrugations of the nonwoven fabric can be adhered highly probability to the elastic members with the adhesive.

Preferably, the nonwoven fabric is folded back at the free end of the leakage preventing wall so that the leakage preventing wall is formed of the two-folded nonwoven fabric, and the elastic member is positioned between the two-folded nonwoven fabric so that the valleys of the corrugations of the nonwoven fabric are positioned on two sides of the elastic member and are individually adhered to the elastic member with the adhesive.

In the invention, however, it may also be possible that the nonwoven fabric is not folded back at the free end of the leakage preventing wall and that the valleys of the corrugations of the nonwoven fabric are positioned on and adhered to only one side of the elastic member.

DESCRIPTION OF THE PREFERRED EMBODIMENTS

Figure 1:
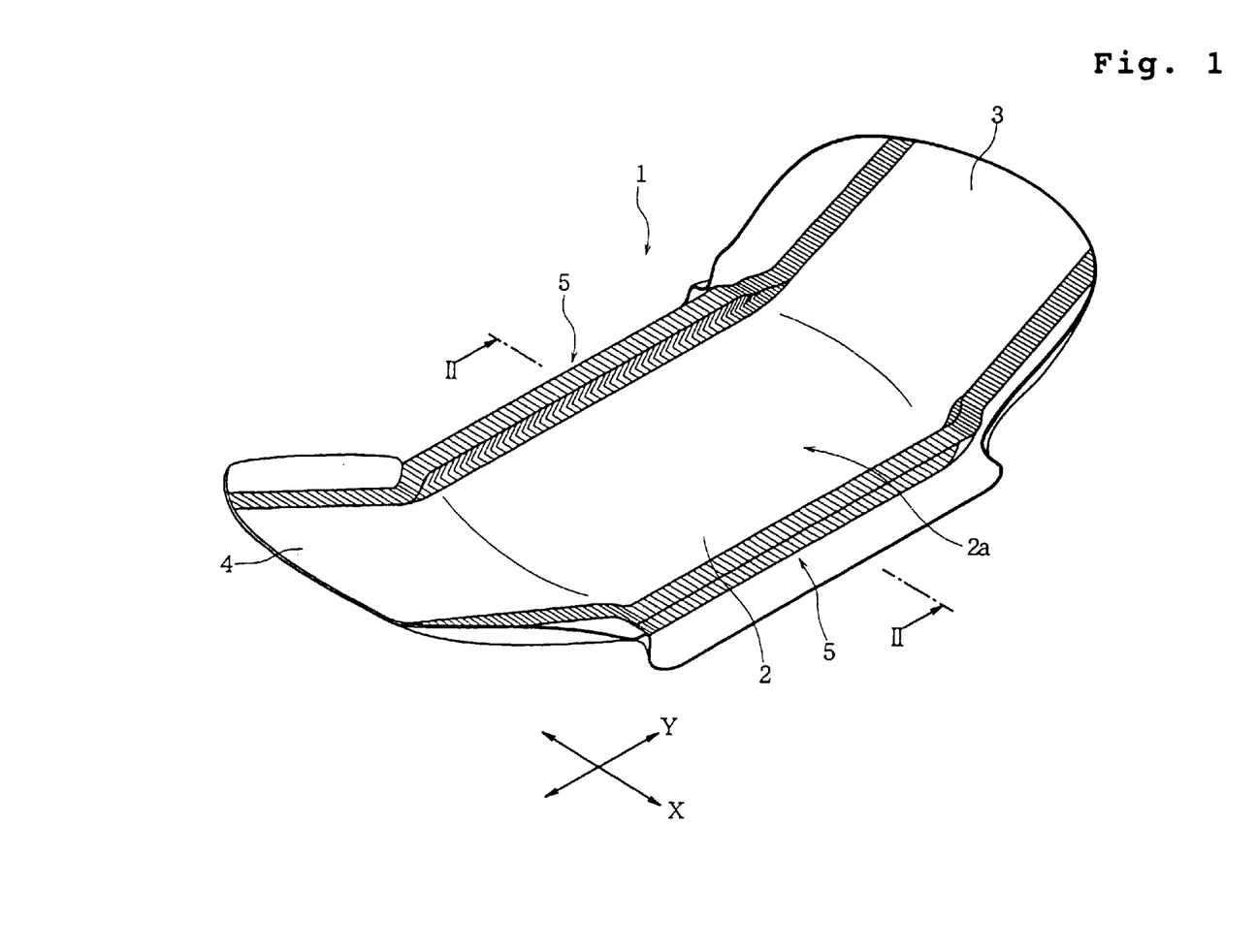
FIG. 1 is a perspective view showing one embodiment of an absorbent article of the invention.
Figure 2:
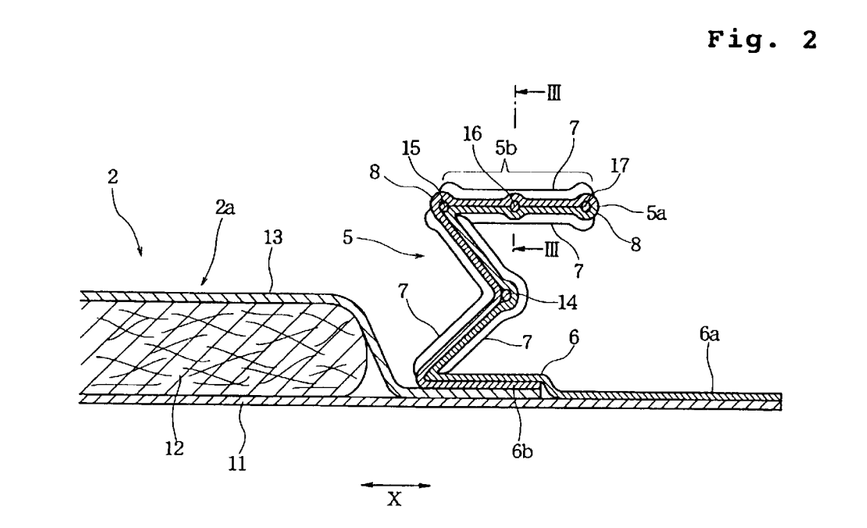
FIG. 2 is a sectional view of a portion taken along line II—II of FIG. 1.
Figure 3:
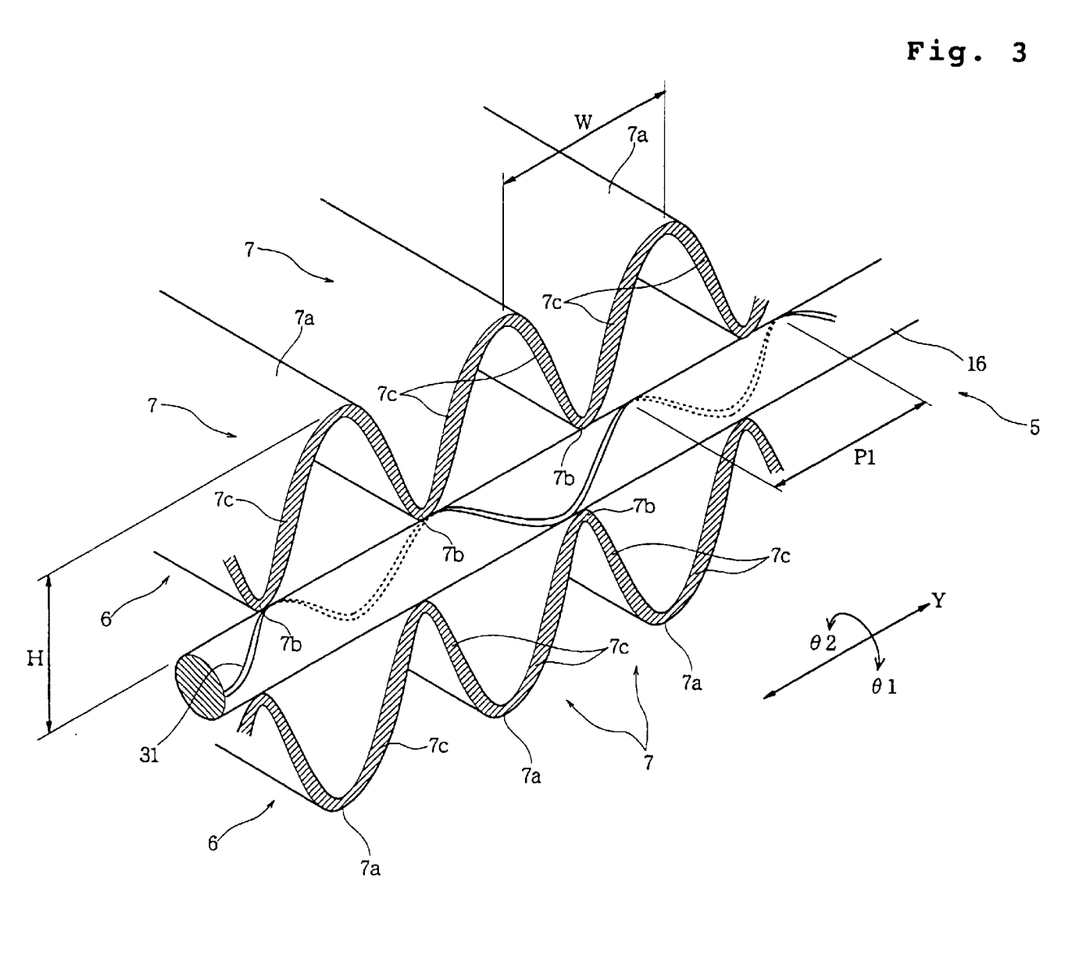
FIG. 3 is a sectional view taken along line III—III of FIG. 2, and shows one mode of embodiment.
Figure 4:
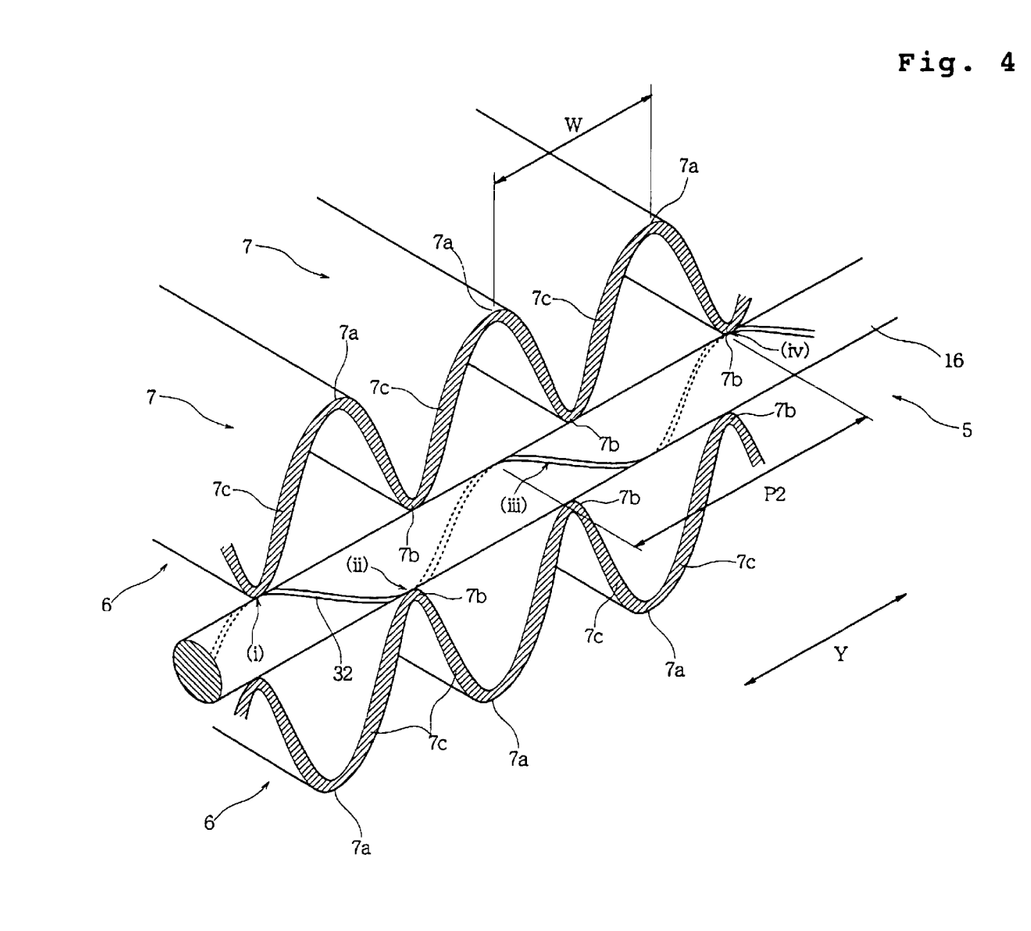
FIG. 4 is a sectional view taken along line III—III of FIG. 2, and shows another mode of embodiment.
Figure 5:
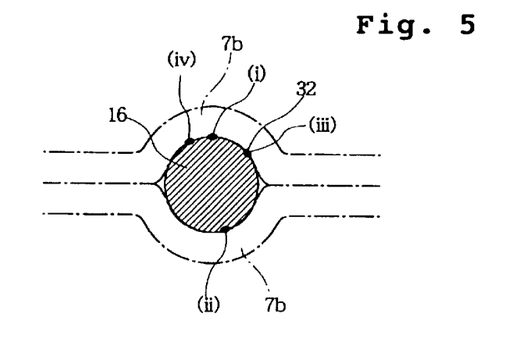
FIG. 5 is a sectional view for explaining the adhered portions between the valleys of corrugated wrinkles and an elastic member.
Figure 6:
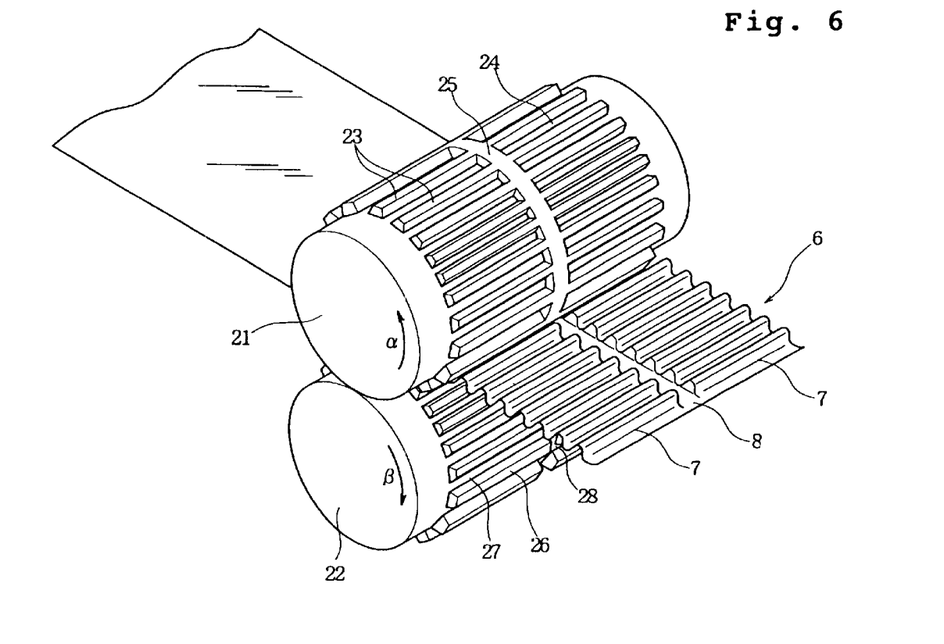
FIG. 6 is a perspective view showing a process for shaping corrugated wrinkles on a nonwoven fabric.

FIG. 1 is a perspective view showing a sanitary napkin as one embodiment of an absorbent article of the invention; FIG. 2 is a sectional view of a portion taken along line II—II of FIG. 1; FIGS. 3 and 4 are sectional views taken along line III—III of FIG. 2 but shows different modes of embodiments; FIG. 5 is a sectional view for explaining the adhered portions between an elastic member and a nonwoven fabric; and FIG. 6 is a perspective view showing one example of a process for manufacturing a nonwoven fabric to form leakage preventing walls.

FIG. 1 shows an absorbent article 1 as one embodiment according to the invention. The absorbent article 1 is embodied in a sanitary napkin, of which the X-direction indicates a transverse direction; and the Y-direction indicates a longitudinal direction. The absorbent article 1 is constructed to include a main body and leakage preventing walls 5 and 5 provided thereon. The main body has a front portion 3 and a rear portion 4, lying opposite one another in the longitudinal direction of the article 1, and a central portion 2 between the front portion 3 and the rear portion 4. On two sides of the main body, lying opposite one another in the transverse direction, provided are the leakage preventing walls 5 and 5 which extend in the longitudinal direction.

These leakage preventing walls 5 and 5 are individually provided with elastic members for exhibiting elastic shrinking forces (or elastic contraction forces) in the longitudinal direction, by which the main body of the absorbent article 1 is curved in the longitudinal direction (i.e., curved with the longitudinally opposed front and rear edges raised upward) and by which the leakage preventing walls 5 and 5 are raised into stereoscopic shapes from the surface 2a of the central portion 2.

As shown in FIG. 2, the main body of the absorbent article 1 is constructed to include: a liquid-impermeable back sheet 11; an absorbent core (or absorbent layer) 12 laid on the back sheet 11; and a liquid-permeable surface sheet 13 covering the absorbent core 12. The absorbent core 12 is disposed to extend from the central portion 2 partially to the front portion 3 and the rear portion 4. The back sheet 11 has a larger width than the surface sheet 13, and both the back sheet 11 and the surface sheet 13 extend outwardly of the absorbent core 12 to have outer peripheral portions, which are bonded to each other with a hot-melt adhesive or are fusion bonded to each other by heat embossing.

The absorbent core 12 can be made of any suitable absorbent materials, such as a mixture of ground pulp and SAP (i.e., superabsorbent polymer) enveloped by a liquid-permeable paper, air-laid pulp treated with a binder into a sheet form, an absorbent paper, and a nonwoven fabric mainly composed of hydrophilic fibers. The back sheet 11 is impermeable to liquid, preferably made of a water vapour-permeable resin film, a nonwoven fabric, or a sheet of a resin film joined with a nonwoven fabric. The surface sheet 13 is permeable to liquid, preferably made of a nonwoven fabric comprising hydrophilic fibers, an apertured nonwoven fabric (i.e., nonwoven fabric having a number of openings), an apertured plastic film (i.e., plastic film having a number of openings), or a laminate sheet of an apertured plastic film and a nonwoven fabric.

The leakage preventing walls 5 are formed of a nonwoven fabric 6 such as a through-air-bonded nonwoven fabric, a point-bonded nonwoven fabric, a spun-bonded nonwoven fabric, a spun-laced nonwoven fabric, a melt-blown nonwoven fabric or an air-laid nonwoven fabric. It is also possible that the leakage preventing walls 5 are formed of a laminate sheet of a plastic sheet such as of ethylene, polypropylene (PP) or the like and a nonwoven fabric. In either case, the leakage preventing walls 5 are preferred to be hydrophobic or water-repellent. Examples of fibers constituting the nonwoven fabric 6 include polyethylene (PE) fibers, polyethylene terephthalate (PET) fibers, and conjugated fibers (i.e., core-sheath fibers or side-by-side fibers) such as those of PE/PP or PE/PET. These fibers are treated to be water-repellent. Preferably, the nonwoven fabric 6 for forming the leakage preventing walls 5 is a spun-bonded nonwoven fabric having a basis weight of from 15 to 40 g/m$^2$ and formed of PE/PP core-sheath fibers having a fineness of from 1.1 to 4.4 dtex.

As shown in Figures, the nonwoven fabric 6 is formed with corrugated wrinkles 7. In the leakage preventing walls 5, the crests and valleys of the corrugated wrinkles 7 are alternated in the longitudinal direction (Y-direction). In more detail, as shown in FIG. 2, the portion of the nonwoven fabric 6, which is folded back and forms the leakage preventing wall 5, has two kinds of areas, one being a corrugated area having the corrugated wrinkles 7 and the other being a plain area (or smooth surface area) 8 having no corrugated wrinkle and located between adjacent corrugated areas.

FIG. 6 is an explanatory view of a process of hot-pressing the nonwoven fabric 6 for forming the corrugated wrinkles 7. Here, for sake of simplicity, only two corrugated areas of the corrugated wrinkles 7 and one plain area 8 therebetween are shown.

In this hot-pressing process, the nonwoven fabric 6 is hot-pressed while being clamped between molding rolls 21 and 22. These molding rolls 21 and 22 rotate in directions α and β respectively, while meshing with each other. The molding roll 21 is provided on its molding face with stripe-embossed molding ribs 23 and grooves 24 which are extended in the axial direction of the roll 21 and which are repeated at a predetermined pitch in the rotating direction (or the α direction). The molding roll 21 is further provided with an outer circumference 25 which is flash with the upper faces of the molding ribs 23 and which is continuous in the rotating direction (or the α direction).

On the other hand, the molding roll 22 is provided on its molding face with stripe-embossed molding ribs 26 and grooves 27 which are extended in the axial direction of the roll 22 and which are repeated at a predetermined pitch in the rotating direction (or the β direction). The molding roll 22 is further provided with an inner circumference 28 which is flash with the bottoms of the grooves 27 and which is continuous in the rotating direction (or the β direction).

As the molding roll 21 and the molding roll 22 rotate in meshing engagement with each other while being fed with the nonwoven fabric 6, their molding ribs 23 and 26 mesh with each other such that the molding ribs 23 of the molding roll 21 come into the grooves 27 of the molding roll 22 whereas the molding ribs 26 of the molding roll 22 come into the grooves 24 of the molding roll 21. At this time, the outer circumference 25 of the molding roll 21 bites into the inner circumference 28 of the molding roll 22.

By this continuous molding, two corrugated areas of the corrugated wrinkles 7 and one plain area 8 are simultaneously formed in the nonwoven fabric 6. In the molded nonwoven fabric 6, as shown in FIGS. 3 and 4, the fibers are heavily compressed at crests 7a and valleys 7b of the corrugated wrinkles 7 but are lightly compressed at intermediate portions 7c. Therefore, the crests 7a and the valleys 7b have a higher density than that of the intermediate portions 7c. The crests 7a and the valleys 7b are preferred to have a density of at least 0.1 g/cm³. The preferred upper limit is 1.0 g/cm³.

In the corrugated wrinkles 7 of the nonwoven fabric 6, the distance W (or the corrugation period) between adjacent crests 7a and 7a is preferred to be 0.5 to 3.0 mm, and the height H between the sheet surface at the crest 7a and the sheet back at the valley 7b is preferred to be 0.1 to 0.5 mm.

As shown in FIG. 2, the nonwoven fabric 6 having the corrugated wrinkles 7 is folded in two at the free end 5a of the leakage preventing wall 5. Moreover, elastic members 14, 15, 16 and 17 are sandwiched between the two-folded nonwoven fabrics 6. Portions 6a and 6b of the nonwoven fabric 6 not forming the leakage preventing wall 5 are joined to the surface of the main body of the absorbent article 1, so as to extend from the root end of the leakage preventing wall 5 toward the side edges of the absorbent article 1. In detail, the portion 6b is adhered to the surface sheet 13, and the portion 6a is adhered to the portion 6b (i.e., adhered to the surface sheet 13 through the portion 6b) and the back sheet 11.

The elastic members 14, 15, 16 and 17 can be made of elastic polyurethane yarns, a molded film mainly of SEBS, foamed filaments or natural rubber filaments.

The nonwoven fabric 6 and the elastic members 14, 15, 16 and 17 are adhered, for example, by extending the individual elastic members 14, 15, 16 and 17 by 1.3 times in the direction along which the crests and valleys of the corrugated wrinkles 7 are repeated (i.e., in the longitudinal direction) and by clamping the elastic members 14, 15, 16 and 17 between the two-folded nonwoven fabric 6.

In the embodiment shown in FIG. 2, the leakage preventing wall 5 is raised from its root end and folded two times to form a generally horizontally extending portion including its free end 5a. In this leakage preventing wall 5, the elastic member 14 is positioned at the firstly folded portion (i.e., midway of the rising portion between the root end and the secondly folded portion); the elastic member 15 is positioned at the secondly folded portion; the elastic member 17 is positioned at the free end 5a; and the elastic member 16 is positioned between the elastic member 15 and the elastic member 17. The generally horizontally extending portion, to which the elastic members 15, 16 and 17 are attached, is referred to as a wearer-facing portion 5b that mainly comes into contact with the skin of a wearer in use. Here, it is preferred that the nonwoven fabric 6 is easily folded into two at the free end 5a of the leakage preventing wall 5 and that the leakage preventing wall 5 thus formed is easily folded at the portion having the elastic member 15 to form the wearer-facing portion 5b. In the leakage preventing wall 5, therefore, the portion having the elastic member 15 (i.e., the free end 5a) and the portion having the elastic member 17 (i.e., the secondly folded portion) are formed of the plain areas 8 of the nonwoven fabric 6, and the elastic members 15 and 17 are adhered to the plain areas 8 with a hot-melt adhesive or the like.

On the other hand, the elastic members 14 and 16 are adhered to the corrugated areas of the nonwoven fabric 6 in which the corrugated wrinkles 7 are formed.

FIGS. 3 and 4 are sectional views taken along line III—III of FIG. 2. In the embodiment shown in FIG. 3, the elastic member 16 is a linearly extending material having a circular or elliptical section, and a hot-melt adhesive 31 is applied in a band or linear shape to the surface of the elastic member 16. It is preferred that the hot-melt adhesive 31 has a width smaller than the diameter of the elastic member 16. It is also preferred that the application area of the adhesive 31 to the surface area of the elastic member 16 is 5 to 30%.

In the embodiment shown in FIG. 3, the adhesive 31 is applied in such an undulating locus that the amplitude is directed perpendicularly to the axial direction of the elastic member 16 (i.e., the longitudinal direction of the absorbent article 1: the Y-direction). For example, the adhesive 31 is applied by reciprocating the minute nozzle of a coater of the hot-melt adhesive in the direction perpendicular to the Y-direction and by feeding the elastic member 16 in the Y-direction while turning it reciprocally in the directions θ1–θ2 on the axis of the Y-direction.

Alternatively, the application may be performed by feeding the elastic member 16 in the Y-direction while turning the minute nozzle circularly and while turning the elastic member 16 reciprocally in the directions θ1–θ2 on the axis of the Y-direction.

Next in the embodiment shown in FIG. 4, the elastic member 16 has a circular or elliptical section, and a hot-melt adhesive 32 is applied in a band or linear shape having a width of 0.05 to 0.3 mm to the surface of the elastic member 16. In FIG. 4, the hot-melt adhesive 32 is applied along a helical locus to the surface of the elastic member 16. For example, this application along the helical locus can be performed by fixing the minute nozzle of the coater for the hot-melt adhesive and by feeding the elastic member 16 in the Y-direction while revolving it in a predetermined direction on the axis of the Y-direction.

If the undulating locus shown in FIG. 3 has a period P1 and if the helical locus shown in FIG. 4 has a period P2, P1>W and P2>W, preferably, P1>2×W and P2>2×W. Moreover, the ratios P1/W and P2/W are at least 2, preferably 3 to 5. Where the distance W is 1.36 mm, for example, the periods P1 and P2 are preferably 5 to 6 mm, and the ratios of P1/W and P2/W of this case are 3.7 to 4.4.

With the applied locus of the hot-melt adhesive 31 or 32 being continuous in the longitudinal direction of the elastic member 16 and with the applied positions being regularly varied along the circumferential direction of the elastic member 16, as shown in FIGS. 3 and 4, the valleys 7b and 7b of the corrugated wrinkles 7 and 7 of the two-folded nonwoven fabric 6, as located on the two sides of the elastic member 16, are adhered in a high probability to the circumference of the elastic member 16 by the adhesive 31 or 32.

FIG. 5 shows the positions at which the elastic member 16 is sandwiched by and adhered to the valleys 7b and 7b of the corrugated wrinkles 7 of the two-folded nonwoven fabric 6, in the embodiment of FIG. 4. By pressing the two-folded nonwoven fabric 6 having the elastic member 16 therebetween from the upper and lower sides, the valleys 7b and 7b envelop the elastic member 16 to some extent (i.e., the valleys 7b and 7b are deformed to extend generally along the circumference of the elastic member 16), as shown in FIG. 5. The contact positions between the nonwoven fabric 6 thus pressed and the adhesive 32 are indicated at (i), (ii), (iii) and (iv) in connection with FIGS. 4 and 5. Specifically, the contact positions (i), (ii), (iii) and (iv) of FIG. 4 correspond to those (i), (ii), (iii) and (iv) of FIG. 5.

Thus, the valleys 7b of the corrugated wrinkles 7 of the nonwoven fabric 6 are highly probably adhered to the elastic member 16 with the adhesive 31 or 32. With the adhesive being thus applied, moreover, even if the two-folded nonwoven fabric 6 is pressed from the upper and lower sides of FIGS. 3 and 4, the inner faces of the crests 7a and the intermediate portions 7c of the corrugated wrinkles 7 are adhered in a low probability to the adhesive 31 or 32. Therefore, the corrugated wrinkles 7 having been once crushed flat by pressing the nonwoven fabric 6 will recover to its corrugated state. As a result, the nonwoven fabric 6 is not solidified with the adhesive at the portion of the leakage preventing wall 5 having the elastic member 16. Since the corrugated wrinkles 7 are left at the portion having the elastic member 16, therefore, the wearer-facing portion 5b of the leakage preventing wall 5 shown in FIG. 2 is softly brought into contact with the skin of a wearer.

Also, the elastic member 14 is adhered to the nonwoven fabric 6 with the same adhesion structure as that shown in FIG. 3 or 4.

In the embodiment shown in FIG. 2, the elastic members 15 and 17 are adhered to the plain areas 8 of the nonwoven fabric 6 not having the corrugated wrinkles 7. However, of course, it is also possible that the nonwoven fabric 6 is formed with the corrugated wrinkles 7 even at the portions to be attached with the elastic members 15 and 17 and that the elastic members 15 and 17 are adhered to the nonwoven fabric 6 with the same adhesion structure as that shown in FIG. 3 or 4. In this case, the corrugated wrinkles 7 are not crushed even at the portions having the elastic members 15 and 17 to provide a soft feel to the skin of a wearer.

Heretofore, the absorbent article of the invention is shown embodied in a sanitary napkin. However, the invention should not be limited to the sanitary napkin but is applicable to any absorbent articles such as disposable diaper, urine pad, or the like. Moreover, although the leakage preventing wall 5 in the foregoing embodiments is raised to have such a cross section as shown in FIG. 2, it should not be limited thereto. For example, the leakage preventing wall of the invention may be of the shape of a "<" or a reversed "L". Alternatively, it may be of the shape rising simply obliquely upward from the surface of the main body of the absorbent article.

Moreover, the adhesive applied on the surface of the elastic member may be of any locus, so long as the adhesive is in a band or linear shape continuous in the axial direction of the elastic member and the adhesive appears regularly or at random at an interval on an arbitrary line which is set on the surface of the elastic member to extend parallel to the axial direction.

According to the absorbent article of the invention, as has been described hereinbefore, even though the elastic member is adhered to the portion of the leakage preventing wall having the corrugated wrinkles, the corrugated wrinkles at the portion having the elastic member are not crushed, so that the absorbent article provides a comfortable touch feel to the skin of a wearer.

Although various exemplary embodiments have been shown and described, the invention is not limited to the embodiments shown. Therefore, the scope of the invention is intended to be limited solely by the scope of the claims that follow.

What is claimed is:

1. An absorbent article comprising:
   a main body including a liquid-permeable surface sheet disposed on its liquid receiving side,
   a back sheet, and
   an absorbent layer sandwiched between the surface sheet and the back sheet; and leakage preventing walls disposed on the liquid receiving side of the main body, the leakage preventing walls extending in a longitudinal direction of the article and lying opposite one another in a transverse direction perpendicular to the longitudinal direction,
   wherein each leakage preventing wall comprises a nonwoven corrugated fabric having crests and valleys that alternate with each other in the longitudinal direction, the nonwover corrugated fabric is provided with an elastic member extending in the longitudinal direction for generating a longitudinal shrinking force, and the elastic member is adhered to alternate valleys of the nonwoven corrugated fabric with an adhesive that is spirally wrapped around a surface of the elastic member in such a manner so as to form an undulating locus that an amplitude is taken in a direction to intersect the longitudinal direction, wherein
   the undulating locus of the adhesive has a period longer than that of corrugations of the nonwoven corrugated fabric.

2. The absorbent article as set forth in claim 1, wherein the period of the undulating locus is greater than twice that of corrugations of the nonwoven corrugated fabric.

3. An absorbent article comprising:
   a main body including a liquid-permeable surface sheet disposed on its liquid receiving side,
   a back sheet, and
   an absorbent layer sandwiched between the surface sheet and the back sheet; and leakage preventing walls disposed on the liquid receiving side of the main body, the leakage preventing walls extending in a longitudinal direction of the article and lying opposite one another in a transverse direction perpendicular to the longitudinal direction,
   wherein each leakage preventing wall comprises a nonwoven corrugated fabric having crests and valleys that alternate with each other in the longitudinal direction, the nonwoven corrugated fabric is provided with an elastic member, extending in the longitudinal direction for generating a longitudinal shrinking force, and the elastic member is adhered to alternate valleys of the nonwoven corrugated fabric with an adhesive that is spirally wrapped around a surface of the elastic member in such a manner so as to form a helical locus which extends in the longitudinal direction while turning around the elastic member, wherein the helical locus of the adhesive has a period longer than that of corrugations of the nonwoven corrugated fabric.

4. The absorbent article as set forth in claims 1 or 3, wherein the nonwoven corrugated fabric is folded back at a free end of the leakage preventing wall so that the leakage preventing wall is formed of a two-folded nonwoven corrugated fabric, and the elastic member is positioned between the two-folded nonwoven corrugated fabric so that valleys of the corrugations of the nonwoven corrugated fabric are positioned on two sides of the elastic member and are individually adhered to the elastic member with the adhesive.

5. The absorbent article as set forth in claim 3, wherein the period of the helical locus is greater than twice that of corrugations of the nonwoven corrugated fabric.

* * * * *